United States Patent [19]
Savage

[11] Patent Number: 5,368,564
[45] Date of Patent: Nov. 29, 1994

[54] STEERABLE CATHETER

[75] Inventor: Steven D. Savage, Brooklyn Center, Minn.

[73] Assignee: Angeion Corporation, Plymouth, Minn.

[21] Appl. No.: 996,090

[22] Filed: Dec. 23, 1992

[51] Int. Cl.$^5$ .................... A61M 37/00; A61N 1/00
[52] U.S. Cl. ........................ 604/95; 607/122
[58] Field of Search .............. 604/95, 280–282; 128/4, 786

[56] References Cited

U.S. PATENT DOCUMENTS

| | | | |
|---|---|---|---|
| 3,437,091 | 4/1969 | Jerushalmi et al. | 128/786 |
| 3,470,876 | 10/1969 | Barchilon | 128/4 |
| 3,618,614 | 11/1971 | Flynn | 604/282 |
| 3,680,544 | 8/1972 | Shinnick et al. | 128/786 |
| 4,236,525 | 12/1980 | Sluetz et al. | 128/786 X |
| 4,576,772 | 3/1986 | Carpenter | 264/154 |
| 4,627,844 | 12/1986 | Schmitt | 604/280 X |
| 4,636,346 | 1/1987 | Gold et al. | 604/280 X |
| 4,765,330 | 8/1988 | Bach . | |
| 4,790,831 | 12/1988 | Skribiski | 604/280 X |
| 4,801,297 | 1/1989 | Mueller | 604/280 |
| 4,850,351 | 7/1989 | Herman et al. | 128/4 X |
| 4,898,577 | 2/1990 | Bodger et al. . | |
| 5,056,517 | 10/1991 | Fenici | 128/786 |
| 5,083,565 | 1/1992 | Parins | 128/786 |
| 5,125,909 | 6/1992 | Heimberger | 604/282 X |
| 5,152,748 | 10/1992 | Chastagner | 604/95 |
| 5,199,950 | 4/1993 | Schmitt et al. | 604/95 |

OTHER PUBLICATIONS

Bard Electrophysiology Price List (Effective Jan. 1, 1991).
The SteeroCath TM Catheter product literature from EP Technologies, Mountain View, Calif. (date unknown).
"Managements' Discussion and Analysis of Financial Condition and Results of Operations", EP Technologies, Mountain View, Calif., front page, and p. 17 of EP Technologies, Inc. Prospectus, Mar. 1993.
Voyagr TM Series Fully Steerable Catheters product literature from CardioRhythm, San Jose, Calif. (date unknown).
Torqr TM Series Electrode Catheters product literature from CardioRhythm, San Jose, Calif. (date unknown).
RF Ablatr TM Fully Steerable Therapeutic Catheters product literature, from CardioRhythm, San Jose, Calif. (date unknown).
Innovations in Electrophysrology product literature and price list from CardioRhythm, San Jose, Calif. (date unknown).

*Primary Examiner*—C. Fred Rosenbaum
*Assistant Examiner*—Frank Wilkens, III
*Attorney, Agent, or Firm*—Patterson & Keough

[57] ABSTRACT

The invention relates to a steering system for a catheter tip. The system includes wire members that extend through a catheter wall that are used to pull a distal portion of the catheter tip. Anchoring members located near the catheter tip connect the distal end of the catheter with wire members. The steering system also contains control members which are located at a proximal portion of the catheter and are used to control the pull on the wire members. Steering enhancement members are also included in the steering system which facilitate the bending of the catheter wall.

25 Claims, 4 Drawing Sheets

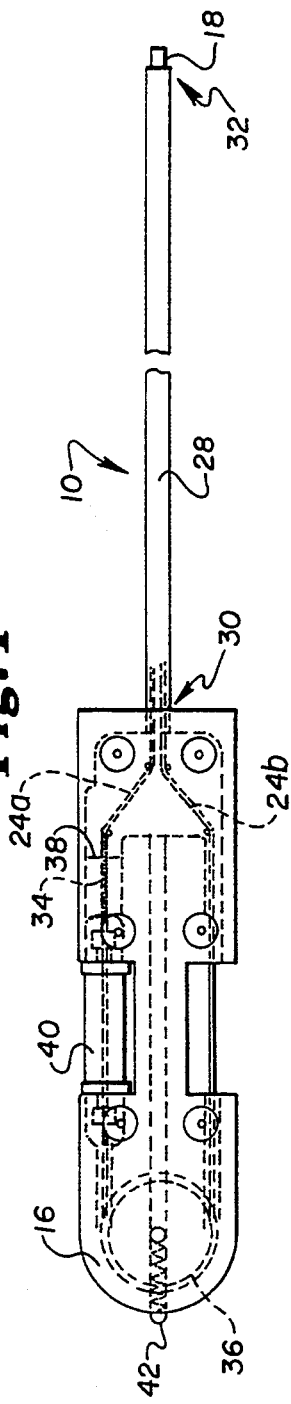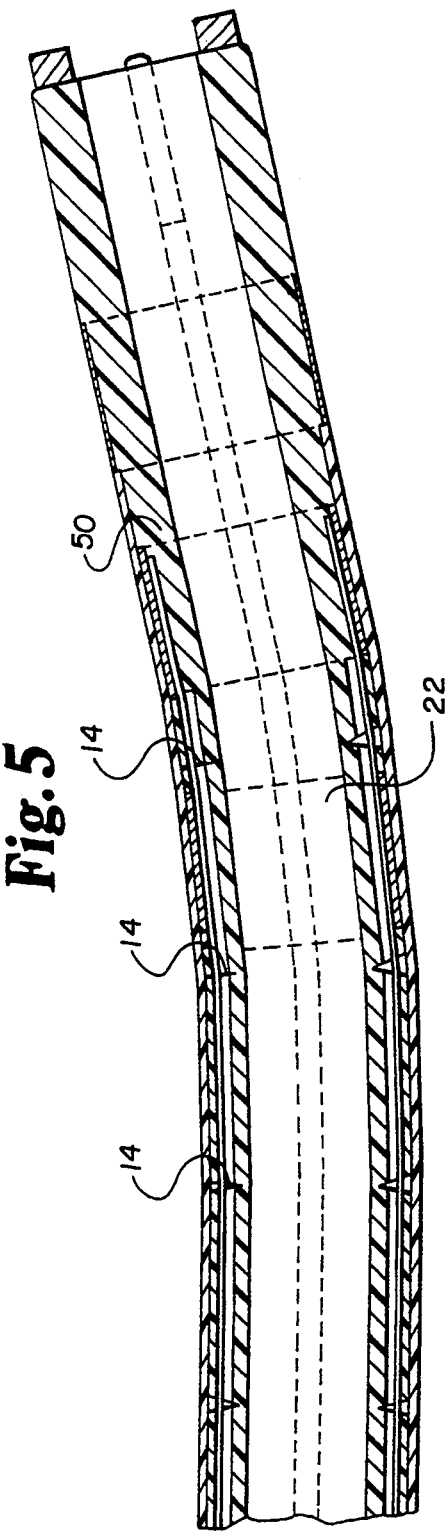

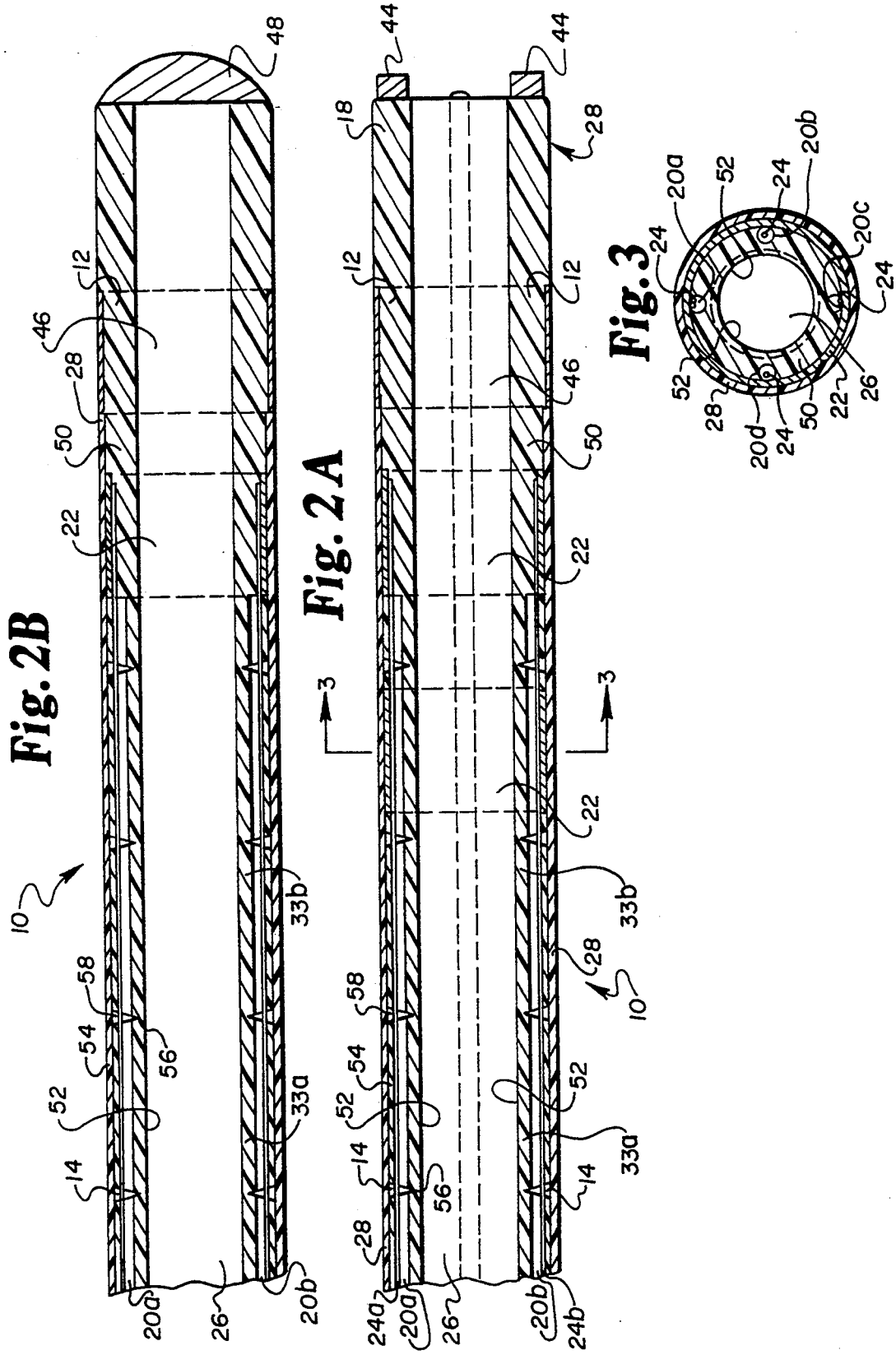

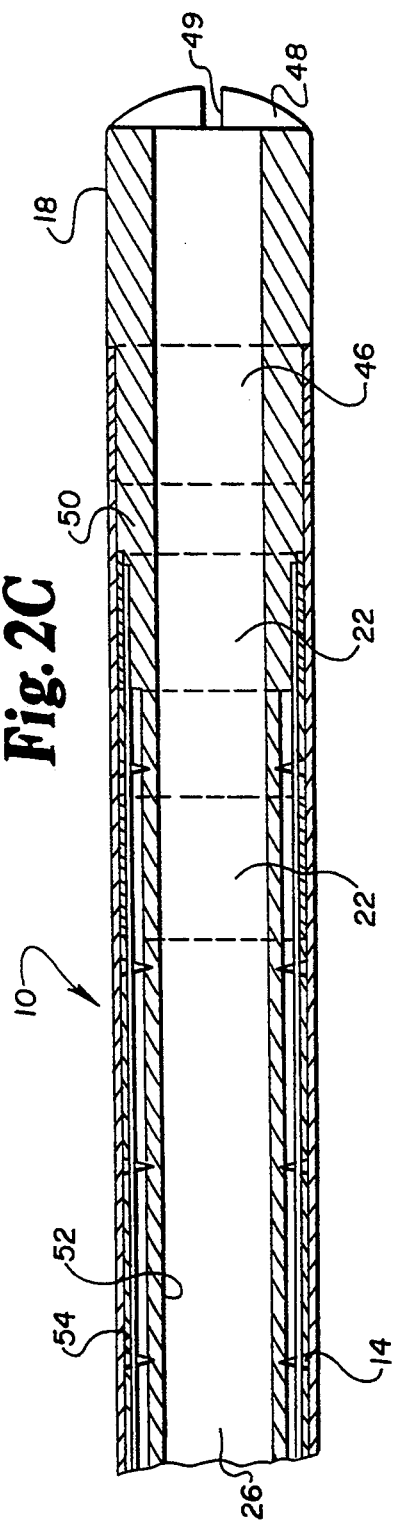

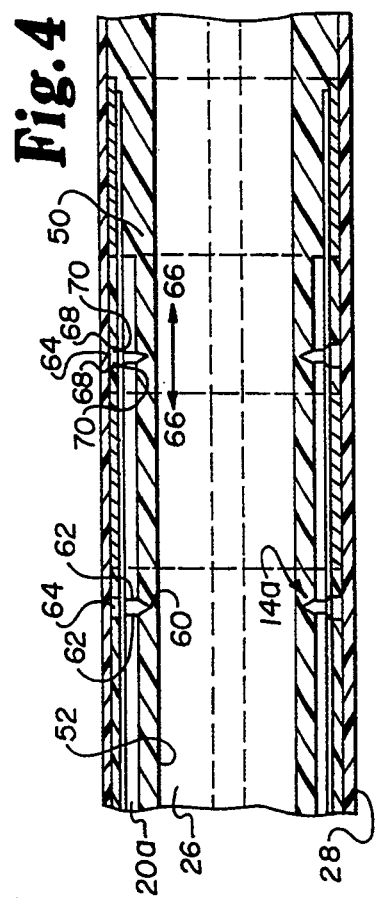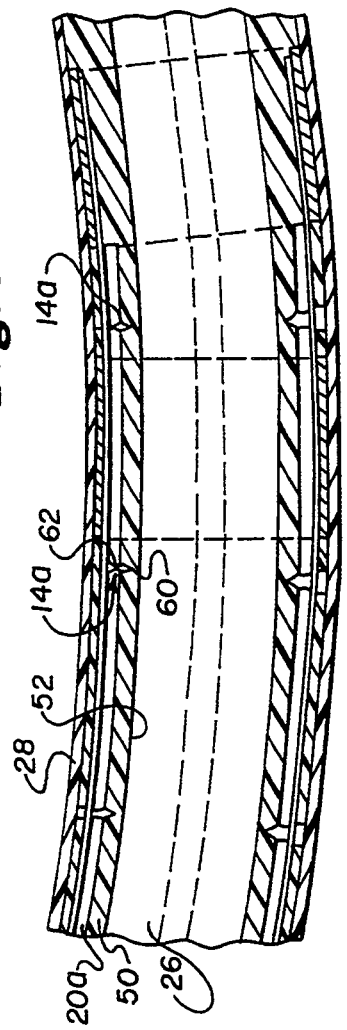

STEERABLE CATHETER

FIELD OF THE INVENTION

This invention relates to a steerable catheter which is utilized in laser surgery. In particular, the invention relates to a steering system for a catheter tip which achieves greater control of the catheter tip movement.

BACKGROUND OF THE INVENTION

Catheters have been utilized in the medical industry for many years. One of the greatest challenges in using a catheter is controlling the position and placement of the catheter tip from a remote location outside of the patient's body. Some catheters have features designed to aid in steering the catheter and overcoming this challenge.

However, several significant problems are still encountered with these catheters. The devices typically have pre-formed inner catheters which are placed in an outer guiding sheath. When the inner catheter is extended or the sheath withdrawn, the inner catheter assumes a different shape. It is usually necessary to draw the inner catheter back into the outer guiding sheath to reshape the catheter tip, and then extend the inner catheter out of the outer sheath for each successive use in another location.

Steerable catheters generally have closed, solid or substantially solid central areas rather than hollow central lumens because of the tendency of lumened steerable catheters to collapse. Since the lumen region is solid, it is not possible to pass another structure, such as a laser catheter, through the steerable catheter.

Steerable catheters exhibit different properties when positioned in a patient's body rather than outside the body. After insertion into the body, the material of the steerable catheter is warmed, and the catheter may absorb water. As a result, the steerable catheter may not perform as desired because of the change in the plastic characteristics.

Also, known steerable catheter distal tips exhibit non-fluid movements. The catheter distal tip often bends with only exaggerated and imprecise movements. A locking cam must be tightened or the handle held in place once the tip is in place during the medical procedure, which also contributes to imprecise movements of the tip. These devices also lack the ability to make very small movements, such as tight radius turns. Also, wire controlled steerable catheters may experience undesired wire deformation over time which affects control.

Torque has also been a significant disadvantage encountered with known steerable catheters. As the steerable catheter travels through the body, different drag forces are created on the catheter. A loss in torque results, and additional power to make the catheter proceed through the body is required.

Another type of steerable catheter uses a bellows which aids in catheter bending. The bellows stretches and collapses as the catheter is moved. However, in steerable catheters having a bellows configuration, the inner surface of a central lumen of the catheter is often configured so that passage of any structure through the central lumen, such as a laser catheter, is impaired.

SUMMARY OF THE INVENTION

The present invention relates to a steerable catheter which includes an elongate catheter body having a circular wall. Wire members extend through the catheter wall to pull on a portion of the catheter wall and the catheter tip. The steerable catheter also includes anchor members located along the length of the catheter body for connection with the distal end of the wire members. A control member located at the proximal end of the catheter is used to control the pull on the wire members. A steering enhancement structure also makes up a part of the steerable catheter, including a portion of the catheter wall having shaped radial indentations which facilitate the bending of the catheter wall. A lumen extends the length of the catheter.

The invention also relates to a steering enhancement structure which improves the maneuverability of a medical catheter. The steering enhancement structure comprises a catheter body which has a catheter wall. A radial indentation region is positioned within the catheter wall.

The invention also relates to a steerable catheter which permits the passage of a biologically compatible fluid comprising a catheter body having a circular wall. A catheter tip and a ring electrode are positioned at the distal end of the catheter body. Wire members extend through the catheter wall to pull on a portion of the catheter wall and the catheter tip. The steerable catheter also includes anchor members located along the length of the catheter body for connection with the distal end of the wire member. A control means is located at the proximal end of the catheter to control the pull on the wire members. A steering enhancement structure also makes up part of the steerable catheter, including a portion of the catheter wall having shaped radial indentations which facilitate the bending of the catheter wall. A lumen extends the length of the catheter. Passage means are located within the catheter tip and the ring electrode for the passage of a biologically compatible fluid.

BRIEF DESCRIPTION OF THE DRAWINGS

FIG. 1 is a side view of the catheter of the present invention.

FIG. 2A is side sectional view of a portion of the catheter.

FIG. 2B is a side sectional view of a portion of an alternate embodiment of the catheter shown in FIG. 2A.

FIG. 2C is a side sectional view of a portion of an alternate embodiment of the catheter shown in FIG. 2A.

FIG. 3 is a sectional view taken along line 3—3 of FIG. 2A.

FIG. 4 is a side sectional view of an alternate embodiment of a steering enhancement means of the catheter.

FIG. 5 is a side sectional view of a portion of the catheter in a bent configuration.

FIG. 6 is a side sectional view of a portion of the catheter in a bent configuration of the alternate embodiment depicted in FIG. 4.

DETAILED DESCRIPTION OF THE INVENTION

The invention is a steerable catheter which is highly maneuverable. The catheter comprises radial indentations in the catheter wall, a large central lumen, and is partially controlled by the pulling and releasing of wire members attached to anchoring rings positioned along the length of the catheter.

Referring to FIGS. 1 and 2A, steerable catheter 10 includes catheter body 12, steering enhancement means or notches 14, platform handle 16, distal tip 18, wire access lumens 20a, 20b, steering or anchoring rings 22, wires 24a, 24b, central lumen 26, and outer sheath 28.

Guiding or outer sheath 28 is positioned over and extend along a length of the catheter body 12 between platform handle 16 and distal catheter tip 18, and is generally circular in cross section. Outer sheath 28 may be attached to catheter body 12. The length of catheter body 12 and the length of outer sheath 28 may vary depending on the distance to the site at which the catheter will be utilized. Outer sheath 28 is preferably made from a biologically compatible thermoplastic material which has some resilience, compression, and elasticity properties. Preferred materials include urethane and nylon elastomers. Outer sheath 28 may be optionally coated with an anti-thrombolytic material. Outer sheath 28 provides structural strength to catheter 10 and also prevents passage of blood or tissue into catheter 10.

Catheter body 12 is generally circular in cross section. Catheter body 12 is preferably made from a biologically compatible thermoplastic material which has some resilience, compression, and elasticity properties. Preferred materials include urethane and nylons. Consecutively softer materials may optionally be utilized along the length of the catheter body 12 as catheter 10 progresses from the proximal end 30 adjacent handle 16 towards distal end 28. Preferably, catheter body 12 material becomes progressively softer and more pliable at distal end 32 with the use of progressively softer, lesser durometer plastic materials, for example portion 33a compared with portion 33b, as shown in FIG. 2A and FIG. 2B. Stiffer, higher durometer plastics are preferably utilized for the main part of catheter body 12.

Platform handle 16, shown schematically in FIG. 1, controls the movement of steerable catheter 10 through the body. Handle 16 may contain a threaded rod 34 and a pulley mechanism 36, shown in FIG. 1, to control the pull on one or more pull wire members 24 and the movement of catheter tip 18. Wires 24a, 24b are positioned adjacent threaded rod 30. Bearing 38 is positioned on one end of threaded rod 34, and knurled knob 40 is positioned along the length of threaded rod 34. A spring or screw 42 is adjacent pulley mechanism 36. Threaded rod 34 locks the position of steerable catheter 10. Exerting pressure on spring or screw 42 actuates wires 24a, 24b giving positive movement of wires 24, so there is less tension on catheter 10. Actuation of wires 24 causes wires 24 to move forward or backwards so that catheter 10 moves in the desired direction. As knob 40 is engaged, rod 34 does not rotate because bearing 38 creates positive locking of catheter tip 18 without use of force. Positive locking is advantageous since it prevents movement of the catheter tip 18 once catheter 10 is positioned at the desired site within the patient. Spring 42 and pulley mechanism 36 keep tension in the system to alleviate any slack in the system. In one embodiment, a thumb screw (not shown) is utilized to move catheter tip 18 forward or backward in the patient's body. Use of this type of system permits catheter 10 to move smoothly and in fluid motion within the patient's body.

Alternatively, platform handle 16 may comprise a servomechanism which pushes and pulls on wires 24 to control the pull on wire members 24 in catheter 10 and the movement of catheter tip 18. Alternatively, handle 16 may comprise a worm gear coupled to another gear. As knob 40 is spun, the worm gear turns, thereby turning pulley mechanism 36 on which wires 24a, 24b are positioned. These systems also provide positive locking of catheter tip 18 in any position, without using any force. Catheter tip 18 remains locked in position until spring or screw 42, the worm gear, or the servomechanism is actuated, turned or engaged.

Referring to FIG. 2A, distal tip 18 is positioned at the distal end 28 of catheter body 12 of steerable catheter 10. A device to administer laser energy may be passed through central lumen 26 of catheter body 12 to tip 18. One or more unipolar or bipolar sensing or tip electrodes 44 may also be positioned within and extend from distal tip 18. Preferably, two to four bipolar tip electrodes 44 extend from distal tip 18 in a perpendicular orientation to the tissue surface. Tip electrodes 44 may be configured to record unipolar or bipolar signals from the tissue, and may be in a bi-planar orientation. A plurality of ring electrodes 46 may also be positioned proximate tip 18 in a parallel orientation to the tissue surface. Tip electrodes 44 and ring electrodes 46 are preferably comprise a metallic material. The invention, however, may be employed in various types of catheters using various catheter tips.

An alternative embodiment of catheter 10 is shown in FIG. 2B. Catheter tip 18 is solid and contains an ablation electrode 48 to administer electric energy to an affected site during the medical procedure. Generally, ablation electrode 48 is made of a metallic material.

In the alternative embodiment of catheter 10 shown in FIG. 2C, catheter tip 18 and one or more ring electrodes 46 are solid with one or more smaller holes or passageways 49 to allow passage of a sterile flushing medium through and around the metallic surface. Tip 18 and ring electrodes 46 are made of a metallic material. Alternatively, tip 18 and ring electrodes 46 may be made of porous metals which may contain a plurality of small passageways 49 connecting the inner and outer surface of the metal, and permitting passage of a sterile flushing medium. In both of these embodiments, the fluid acts as a medium to bathe the catheter elements crucial to mapping and ablation, allowing them to remain free of coagulated biological materials which can alter their inherent effectiveness. This enhances mapping efficiency. In addition, the fluid is particularly important in medical procedures such as cardiac ablation in which the temperature of the metal parts of the catheter can be elevated, since the fluid reduces the temperature of the metal parts.

Referring again to FIG. 2A, wire access lumens 20a, 20b–20n extend along the length of steerable catheter 10, from platform handle 16 to tip 18, and are preferably formed with extrusion techniques. Wire access lumens 20 are generally circular in cross section and are positioned within catheter wall 50 of catheter body 12 of steerable catheter 10. In general, two to four wire access lumens are positioned preferably coaxially within catheter wall 50, although additional lumens are possible. However, due to the tendency of a multiple lumen catheter to collapse, the catheter may include a braided material to enhance structural integrity. A non-flow material, such as a plastic or metallic material, may be inserted into the multiple lumens when an outer jacket or outer sheath is positioned over the braid and the multiple lumen catheter tube. The lumens will not collapse and a circular identity will be retained when this is done. The inserted metal or plastic material is withdrawn after the outer sheath is formed. A standard thermoplastic elastomer may be used for the inner lumen. A layer of a lubricous material, such as a TEFLON braid material, may be applied to the device as a post-manufacturing step.

Strengthening members may be optionally employed and positioned between notches 14 to stiffen catheter wall 50. Strengthening members may optionally be positioned in only a selected portion of the catheter wall. Circular strengthening members provide support for and retain the circular integrity of steerable catheter 10, especially when catheter 10 is in a bent state or when catheter 10 includes multiple wire access lumens. Strengthening members may include springs, metallic rings, thickened areas of catheter wall material, or different choices of materials so that some portions of catheter wall 50 include a softer or a harder material, such as a plastic.

Wires 24a, 24b–24n are movably positioned within wire access lumens 20. Multiple wires 24 may be utilized within each wire access lumen 20 and there may be numerous lumens 20, as shown in FIG. 3. The length of wires 24a, 24b depend on the steering or anchoring ring 22 to which they are each attached. Wires 24 may have some elastic properties and may be made from a high tensile strength material such as 304 V wire, a stainless steel wire manufactured by a medical wire manufacturer, such as Fort Wayne Metals. Preferably, a wire having two times the standard wire tensile strength is utilized. However, any elasticity must be resilient and predictable to ensure restoration to original lengths and to ensure precise bending of the catheter during successive uses of the wires.

Steering or anchoring rings 22 are generally circular in cross section and are positioned within catheter wall 50 of steerable catheter 10. Steering rings 22 extend around the circumference of catheter 10. A plurality of steering rings 22 may be positioned at various locations along the length of catheter 10. Preferably, steering rings 22 made from a metallic material such as stainless steel are utilized in steerable catheter 10. Wires 24 are attached at the distal end to steering ring 22 or tip 18, and at the proximal end to platform handle 16. Wire 24 attached to a steering ring 22 permits catheter 10 to bend and to be maneuvered along the length of catheter 10 as wires 24 are pulled. This construction is not limited to only maneuvering distal tip 18, but also to providing steerability to other parts of catheter 10. Wires 24 are preferably silver soldered to steering ring 22 although other connection means may be utilized.

Referring to FIG. 3, an end section view of catheter 10 is shown. Catheter wall 50 is preferably thin, comprising a substantially small percentage of the diameter of catheter 10. Preferably, catheter wall 50 is approximately 0.01 inches in thickness although sizes will vary based upon the desired use. Notches 14 are positioned within catheter wall 50. Wire access lumens 20a, 20b, 20c, 20d containing wires 24a, 24b–24n are positioned within catheter wall 38 of catheter 10. The interior surface 52 of catheter wall 50 defines a substantially straight central lumen 26, and surface 52 is preferably smooth and continuous, without segmentation. Central lumen 26 is substantially open, comprising a relatively large percentage of the diameter of catheter 10. Preferably, at least fifty percent (50%) of the outer diameter of catheter 10 comprises central lumen 26, and most preferably, eighty percent (80%) of the outer diameter of catheter 10 comprises central lumen 26. For instance, in a six french catheter 10, central lumen 26 may be approximately four french in size. However, these ratios may vary. Central lumen 26 may be used to insert other types of catheters through catheter 10 without removal of catheter 10, as shown in FIG. 2A. Therefore, catheter 10 acts as a guiding catheter through which other catheters may be inserted. It is preferable that surface 52 be smooth so that other catheters may be easily passed through lumen 26.

FIGS. 2A, 2B, 2C, and 5 show how steering enhancement means or notches 14 are positioned along a length of catheter wall 50 between outer surface 54 and interior surface 52 of catheter wall 50. Preferably, notches 14 are radial indentations in catheter wall 50. As shown in FIGS. 2 and 4, notches 14 may be varied in shape, such as V-shaped indentations, or multiple fulcrumed configurations. Notches 14 may be molded into catheter wall 38 or may be metal rings, or other structures. Notches 14 may be spaced at either regular or irregular positions along the length of catheter wall 50, and preferably extend around the entire diameter of catheter wall 50. Alternatively, notches 14 may be positioned on the side of catheter 10 to be compressed, with strengthening members positioned on the opposite side of catheter 10.

Notches 14, which are non-linear V-shaped slots or angled wedge indentations, include narrow apex 56 adjacent interior surface 52 and a wider top opening 58 adjacent outer surface 44 of catheter wall 50. Top opening 58 is approximately 0.305 mm (0.012 inches) in width, although the width of opening 58 may vary. Notch 14 is approximately 0.305 mm to 0.381 mm (0.012 to 0.015 inches) in length axially. Apex 56 does not completely extend to interior surface 52. There is an approximate 0.254 mm to 0.381 mm (0.010 to 0.015 inches) space or gap between apex 56 and interior surface 52, although this may vary. The material comprising catheter wall 50 may be a softer material composition proximate apex 56 and a stiffer material composition proximate top opening 58. Catheter wall material is removed to form notches 14 when notches 14 are molded in catheter wall 50. As a result, notches 14 provide a means for taking up the catheter material as notches 14 are compressed and catheter 10 is bent. The area between notches 14 is thicker since the area comprises more catheter wall material which may be used as a strengthening member for catheter 10.

Notches 14a, shown in FIG. 4, include apex 60, fulcrumed non-linear walls 62, and wide top opening 64, and are positioned within catheter wall 50. Apex 60 is adjacent interior surface 52 of catheter wall 50, but there is approximately 0.010 inches between apex 60 and interior surface wall 52, although this may vary. Fulcrumed walls 62 are concave and semi-spherical, and are positioned between wires 24 and interior surface 52. Top opening 64, adjacent outer surface 54 of catheter wall 50, is approximately 0.305 mm (0.012 inches) in width, although this may vary. Notches 14a are approximately 0.305 mm to 0.381 mm(0.012 to 0.015 inches) in length axially.

The slot size, or amount of catheter wall material removed, of notches 14 may also vary among different notches, and is determined by the application for which catheter 10 is utilized. In addition, the width of top opening 58, 64, slot size of notches 14, 14a and the spacing of the notches determine the ease of bending catheter 10. If the width of the opening 58, 64 of slot or notch 14, 14a and the slot size of notch 14, 14a is very small, outer sheath 28 will bend very little. Close spacing of notches 14, 14a allows catheter 10 to bend in more locations and in a tighter radius. Notches 14, 14a allow catheter 10 to bend more with exertion of less force, relative to other catheters, while retaining the circular identity of catheter 10.

In addition, the slot opening width and spacing of notches 14, 14a may be utilized to prevent over-bending or collapsing of inner lumens in catheter 10, such as wire access lumens 20. Preferably, the slot top opening width of notches 14 and the spacing of notches 14 are such that when catheter 10 is in a bent configuration, the notches 14 close in a direction in which catheter 10 is bent, as shown in FIG. 5. In the alternative embodiment shown in FIG. 4, the fulcrum configuration of the walls of notch 14a results in the compression being dissipated outwardly at apex 60, as indicated by the arrows 66. The top edges 68 of notch 14a come together to close the notch opening 64 of notch 14a as catheter 10 is bent. Notch opening 64 is subjected to tension forces when catheter 10 is in a bent configuration as indicated by the arrows 70 in FIG. 4. The tension created in bending catheter 10 causes top edges 68 and fulcrumed walls 62 of notch 14a to be compressed toward one another in the direction in which catheter 10 is bent, as shown in FIG. 6.

The catheter of the present invention may function as a steerable guiding and mapping catheter. A surgical catheter, such as a laser catheter, may be inserted through central lumen 26 to a target site to perform a surgical procedure. In another configuration, catheter 10 may itself be used to locate particular tissue during a surgical procedure and then destroy the tissue as needed if an ablation electrode is used, without the insertion of another catheter. Steerable catheter 10 is especially useful in electrophysiology applications, although catheter 10 may be used in a wide variety of medical procedures.

In operation, catheter 10 is inserted into the patient. The cardiologist or other user of catheter 10 controls the direction of catheter 10 distal tip 18 using platform handle 16 to apply tension on selected wires 24a, 24b which are attached to steering rings 22. If a wire positioned in wire access lumen 20a is pulled, catheter tip 18 will bend in a particular direction adjacent the steering ring 22 to which the selected wire is attached. If a wire positioned in wire access lumen 20b is pulled, catheter 10 will bend in another direction. Steering enhancement means, such as the above notches 14, 14a, greatly aid in the movement, bending, and control of catheter 10. Undesired compression of wire access lumens 20 is reduced or eliminated by these novel notch configurations. The ability to pull wires 24 at different sites of steering rings 22 along the length of catheter 10, coupled with the additional pliability provided by the notches, results in improved, smooth maneuverability, control, and steerability of the catheter within the patient's body. The ability to lock catheter tip 18 in position is also advantageous to the smooth control of catheter 10 since it reduces the user intervention of applying force to the knob, holding the handle in place or locking a cam during the medical procedure.

Catheter 10 with notches 14, 14a provides improved repeatability and has an active return capability so that the device does not rely solely on the resilience of the catheter material to return to its previous position. Since catheter 10 is pulled at various points along its length, rather than only at its distal end or tip, there is less stress on the catheter material because there is less torque. As a result, the operator can maneuver the catheter by pulling back on the wires knowing that the catheter will respond in the same way each time the catheter is pulled a certain distance. Thus, the catheter has a longer life expectancy and the elasticity of the catheter 10 is preserved for a longer period of time.

The speed and fineness of control of catheter 10 is also a distinct advantage of this invention. Bends are made quicker because of the ability to bend catheter 10 throughout much of the entire length of catheter 10. As a result, the operator has more control of catheter 10. Also, catheter 10 may be positioned much more quickly than other steerable catheters since it is not necessary to bring the catheter tip into and out of an outer sheath for shaping purposes. This may also reduce the occurrence of trauma to endothelial linings within arteries or other structures. In addition, when catheter 10 is used as a guiding catheter, a significant time savings results since a different type of catheter may be inserted without requiring removal of the guiding catheter and re-location of the affected tissue with a second catheter. In addition, the straight, continuous central lumen provides an easy passage of the other catheter through catheter 10 without the other catheter getting caught in or hooked on an irregularly shaped central lumen surface.

The catheter may also have a balancing and sensing sub-system for monitoring wire elongation. The sub-system determines the stress on the wires and may compensate for any deformation of wire or catheter body material which may develop after repeated use of the catheter.

I claim:

1. A steerable wire guiding catheter comprising:
   a) an elongate catheter body having a generally circular catheter wall, a distal end, and a proximal end, the circular catheter wall being comprised of a generally tubular body presenting an interior surface and an outer surface;
   b) a plurality of wire means, each wire means having a proximal end and a distal end and extending through the tubular body of the catheter wall for pulling on a steerable portion of the catheter wall proximate the distal end of the catheter body to effect steering of the catheter;
   c) a plurality of anchor means, each anchor means corresponding to a distal end of one of the wire means and axially located along the steerable portion of the catheter wall of the catheter body for connection with a distal end of the respective one of the wire means, at least two of the anchor means being located at axially different positions along the steerable portion of the catheter wall; and
   d) control means located at a proximal portion of the catheter for controlling the pulling on the proximal end of the wire means.

2. The steerable catheter of claim 1 further comprising:
   e) a lumen wall within the catheter body defining a lumen that occupies a substantial portion of the axial cross-section of the catheter and continuously extends along an axial length of the catheter.

3. The steerable catheter of claim 1 wherein the steerable portion of the catheter wall proximate the distal end of the catheter body is integral with the catheter body.

4. The steerable catheter of claim 1 further comprising steering enhancement means within the steerable portion of the tubular body of the catheter wall for facilitating the bending and steering of the catheter.

5. The steerable catheter of claim 4 wherein the steering enhancement means comprises radial indentations within the catheter wall.

6. The steerable catheter of claim 5 wherein the radial indentations comprise V-shaped indentations.

7. The steerable catheter of claim 5 wherein the radial indentations comprise multiple fulcrumed walls.

8. The steerable catheter of claim 2 wherein the lumen of the catheter is suitable for receiving a device therethrough, such that the catheter acts as a guiding catheter.

9. The steerable catheter of claim 1 further comprising electrode means extending from the distal end of the catheter body for sensing and receiving unipolar and bipolar signals from tissue of the patient.

10. The steerable catheter of claim 4 wherein the steering enhancement means comprises placement of a softer material composition proximal the interior surface of the catheter wall along the steerable portion of the catheter wall and a stiffer material adjacent the outer surface along the steerable portion of the catheter wall.

11. The steerable catheter of claim 1 wherein the the catheter body is comprised of a softer material at the distal end of the catheter and a stiffer material at the proximal end of the catheter.

12. A medical catheter having improved maneuverability, comprising:
a) a catheter body having a catheter wall, a distal end, and a proximal end, the catheter wall being comprised of a generally tubular body presenting an interior surface and an outer surface; and
b) a radial indentation region in the tubular body of the catheter wall proximate the distal end of the catheter body, the radial indentation region comprising a plurality of radial indentations extending between and not intersecting the outer surface and the interior surface of the catheter wall.

13. The medical catheter of claim 12 wherein each of the plurality of radial indentations has a first wall and a second wall, a first end and a second end, and an axial length.

14. The medical catheter of claim 13 wherein the first and second walls are are not parallel to each other.

15. The medical catheter of claim 13 wherein at least some of the plurality of radial indentations have a wider opening at the first end and an apex at the second end.

16. The medical catheter of claim 13 wherein the first end of at least some of the plurality of radial indentations compresses more than the second end.

17. The medical catheter of claim 13 wherein at least some of the plurality of radial indentation comprise different materials along the axial length of the radial indentation.

18. The medical catheter of claim 15 wherein a soft material is placed proximate the apex and a stiff material is placed proximate the wider opening of the radial indentation.

19. The medical catheter of claim 14 wherein the first wall and the second wall of the radial indentations comprise V-shaped indentations.

20. The medical catheter of claim 14 wherein the first wall and the second wall of the radial indentations comprise multiple fulcrumed walls.

21. A medical catheter having improved maneuverability, comprising:
(a) a catheter body having a catheter wall, a distal end, and a proximal end, the catheter wall being comprised of a generally tubular body presenting an interior surface and an outer surface; and
(b) a steering enhancement indentation region in the tubular body of the catheter wall proximate the distal end of the catheter body, the steering enhancement indentation region comprising a plurality of circumferential indentations within the catheter wall arranged so that the catheter wall in each region comprises varying durometers, each of the plurality of indentations comprising a material composition having mechanical characteristics differing from the characteristics of the adjacent indentation, the plurality of indentations extending between and not intersecting the outer surface and the interior surface of the catheter, the indentation region comprising locations having a material composition that is more pliable than portions of the tubular body proximate the interior surface of the catheter wall and locations having a material composition that is less pliable than other portions of the tubular body proximate the outer surface of the catheter wall.

22. The medical catheter of claim 21 wherein the catheter body is comprised of a softer material at the distal end of the catheter and a stiffer material at the proximal end of the catheter.

23. A steerable wire guiding catheter comprising:
(a) an elongate catheter body having a catheter wall, a distal end, and a proximal end, the catheter wall comprising a generally tubular body presenting an interior surface and an outer surface, the catheter body comprising a distal portion having a plurality of durometers progressing from the proximal end of the distal portion to the distal end of the catheter body to provide increased pliability proximate the distal end;
(b) a plurality of wire means, each wire means having a proximal end and a distal end and extending through the tubular body of the catheter wall for pulling on a steerable portion of the catheter wall proximate to the distal end of the catheter body to effect steering of the catheter;
(c) a plurality of anchor means, each anchor means corresponding to a distal end of at least one of the wire means and axially spaced along the steerable portion of the catheter wall of the catheter body for connection with a distal end of the respective one of the wire means; and
(d) control means located at a proximal portion of the catheter for controlling the pulling on the proximal end of the wire means.

24. The catheter of claim 23 wherein the plurality of wire means pulls on a steerable portion of the catheter wall integral with and proximate to the distal end of the catheter body.

25. The catheter of claim 23 further comprising radial placement of a material composition stiffer than the tubular body proximate the interior surface and a material composition softer than the tubular body proximate the outer surface of the catheter wall.

* * * * *

UNITED STATES PATENT AND TRADEMARK OFFICE
CERTIFICATE OF CORRECTION

PATENT NO. : 5,368,564
DATED : November 29, 1994
INVENTOR(S) : Savage

It is certified that error appears in the above-indentified patent and that said Letters Patent is hereby corrected as shown below:

IN THE ABSTRACT:

The invention relates to a steering system for a catheter tip. The system includes wire members that extend through a catheter wall that are used to pull a distal portion of the catheter tip. Anchoring members located near the catheter tip connect the distal end of the catheter with wire members. The steering system also contains control members which are located at a proximal portion of the catheter and are used to control the pull on the wire members. A steering enhancement indentation region is also optionally included in the steering system which facilitates the bending of the catheter wall. The indentation region comprising a plurality of indentations extending between and not intersecting the outer surface and the interior surface of the catheter wall.

Column 1, Line 48 change "fight" to --tight--

Column 4, Line 21 change "comprise a" to --comprised of a--

Column 6, Line 57 change "mm(0.012 to 0.015 inches)" to --mm (0.012 to 0.015 inches)--

UNITED STATES PATENT AND TRADEMARK OFFICE
CERTIFICATE OF CORRECTION

PATENT NO. : 5,368,564
DATED : November 29, 1994
INVENTOR(S) : Savage

It is certified that error appears in the above-indentified patent and that said Letters Patent is hereby corrected as shown below:

IN THE CLAIMS:

Column 8, Line 35 change "a)" to --(a)--

Column 8, Line 40 change "b)" to --(b)--

Column 8, Line 42 change "wall" to --wall,--

Column 8, Line 46 change "c)" to --(c)--

Column 8, Line 48 change "the" to --a--

Column 8, Line 54 change "d)" to --(d)--

Column 8, Line 54 change "means" to --means,--

Column 8, Line 55 change "catheter" to --catheter,--

Column 8, Line 59 change "e)" to --(e)--

Column 9, Line 18 change "the" to --a--

Column 9, Line 27 change "wherein the the" to --wherein the--

UNITED STATES PATENT AND TRADEMARK OFFICE
CERTIFICATE OF CORRECTION

PATENT NO. : 5,368,564
DATED : November 29, 1994
INVENTOR(S) : Savage

It is certified that error appears in the above-indentified patent and that said Letters Patent is hereby corrected as shown below:

IN THE CLAIMS:

Column 9, Line 33 change "a)" to --(a)--

Column 9, Line 37 change "b)" to --(b)--

Column 9, Line 48 change "are are not parallel" to --are not parallel--

Column 10, Line 46 change "wall" to --wall,--

Column 10, Line 53, change "body" to --body,--

Signed and Sealed this

Eighteenth Day of July, 1995

*Attest:*

BRUCE LEHMAN

*Attesting Officer*  *Commissioner of Patents and Trademarks*